(12) United States Patent
Clow et al.

(10) Patent No.: US 11,446,134 B2
(45) Date of Patent: Sep. 20, 2022

(54) SUTURE GUIDE DEVICES FOR PREPARING TENDON GRAFTS AND METHODS INCORPORATING THE SAME

(71) Applicant: Community Blood Center, Kettering, OH (US)

(72) Inventors: Andrew Clow, South Charleston, OH (US); Mark Martin, Kettering, OH (US); Laura Steele, Kettering, OH (US)

(73) Assignee: COMMUNITY BLOOD CENTER, Kettering, OH (US)

( * ) Notice: Subject to any disclaimer, the term of this patent is extended or adjusted under 35 U.S.C. 154(b) by 257 days.

(21) Appl. No.: 16/799,225

(22) Filed: Feb. 24, 2020

(65) Prior Publication Data

US 2021/0259822 A1    Aug. 26, 2021

(51) Int. Cl.
*A61F 2/08* (2006.01)
*A61B 17/04* (2006.01)

(52) U.S. Cl.
CPC ............ *A61F 2/08* (2013.01); *A61B 17/0482* (2013.01); *A61F 2240/001* (2013.01)

(58) Field of Classification Search
CPC .... A61F 2/08; A61F 2/0811; A61F 2240/001; A61B 17/0482; A61B 17/00; A61B 2017/1121; A61B 17/1714; A61B 17/04
See application file for complete search history.

(56) References Cited

U.S. PATENT DOCUMENTS

| | | | |
|---|---|---|---|
| 5,623,931 A | 4/1997 | Wung et al. | |
| 5,758,650 A | 6/1998 | Miller et al. | |
| 6,322,571 B1 | 11/2001 | Adams | |
| 6,758,817 B1 | 7/2004 | Pruter et al. | |
| 7,615,062 B2 | 11/2009 | Deland | |
| 9,993,332 B2 | 6/2018 | Woodruff et al. | |
| 2010/0222792 A1 | 9/2010 | Barnes et al. | |
| 2016/0128719 A1 | 5/2016 | Cermak | |
| 2017/0172725 A1 | 6/2017 | Gustafson | |
| 2017/0239037 A1 | 8/2017 | Shino et al. | |
| 2018/0036002 A1 | 2/2018 | Chen et al. | |
| 2019/0374330 A1* | 12/2019 | Beaulier | .......... A61B 17/06166 |

FOREIGN PATENT DOCUMENTS

| | | |
|---|---|---|
| CN | 201775644 U | 3/2011 |
| CN | 107802301 A | 3/2018 |

OTHER PUBLICATIONS

Rawson et al., "Suture Techniques For Tendon Repair; A Comparative Review", Muscles, Ligaments and Tendons Journal 2013; 3 (3): 220-228.

* cited by examiner

*Primary Examiner* — Jennifer Dieterle
*Assistant Examiner* — Rebecca Lynee Zimmerman
(74) *Attorney, Agent, or Firm* — Dinsmore & Shohl LLP (57) ABSTRACT

A graft preparation system that includes a base, a guide extending laterally outward from the base and including a top interface and a bottom interface that removably receives a graft thereon, and a plurality of slots extending through the guide between the top interface and the bottom interface. Each slot of the plurality of slots are sized to receive a needle therethrough such that the plurality of slots form a plurality of channels from the top interface to the bottom interface. The guide is configured to facilitate placement of a suture attached to the needle from the top interface into at least one of the channels formed by the plurality of slots such that the suture is received through the graft at the bottom interface.

20 Claims, 4 Drawing Sheets

SUTURE GUIDE DEVICES FOR PREPARING TENDON GRAFTS AND METHODS INCORPORATING THE SAME

TECHNICAL FIELD

The present invention generally relates to devices for preparing tendon grants augmented with sutures, and more specifically to suture guide devices that facilitate a uniform placement, spacing, tensioning and fixation of a tendon graft for use in a medical procedure.

BACKGROUND

Tendon grafts are generally utilized in various medical procedures, such as clinical orthopedic applications like anterior cruciate ligament replacements. Sutures may be utilized to augment the tendon graft to improve a placement, spacing, tensioning and fixation of the graft, however, suturing a tendon graft during a medical procedure is generally time consuming and labor intensive. Additionally, manually suturing a tendon graft with, for instance, a ruler to determine a suture placement and spacing may result in inconsistent suture patterns along the particular tendon graft being prepared and between multiple tendon grafts formed by a similar method of preparation.

Accordingly, a need exists for a device that may provide guiding features for preparing pre-sutured tendon grafts with consistent and repeatable suture patterns.

DETAILED DESCRIPTION

Reference will now be made in detail to various embodiments of graft preparation systems including a base and a suture guide for forming pre-sutured tendon grafts. Whenever possible, the same reference numerals will be used throughout the drawings to refer to the same or like parts. Directional terms as used herein—for example upper, lower, inner, outer, top, bottom, side, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise. Thus, for example, reference to "a" component includes aspects having two or more such components, unless the context clearly indicates otherwise.

As used herein, the terms "horizontal," "vertical," "distal," "proximal," "longitudinal" and "lateral" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present invention and the embodiments thereof to be described herein may be used in any desired orientation. Moreover, horizontal and vertical walls need generally only be intersecting walls, and need not be perpendicular.

Figure 1:
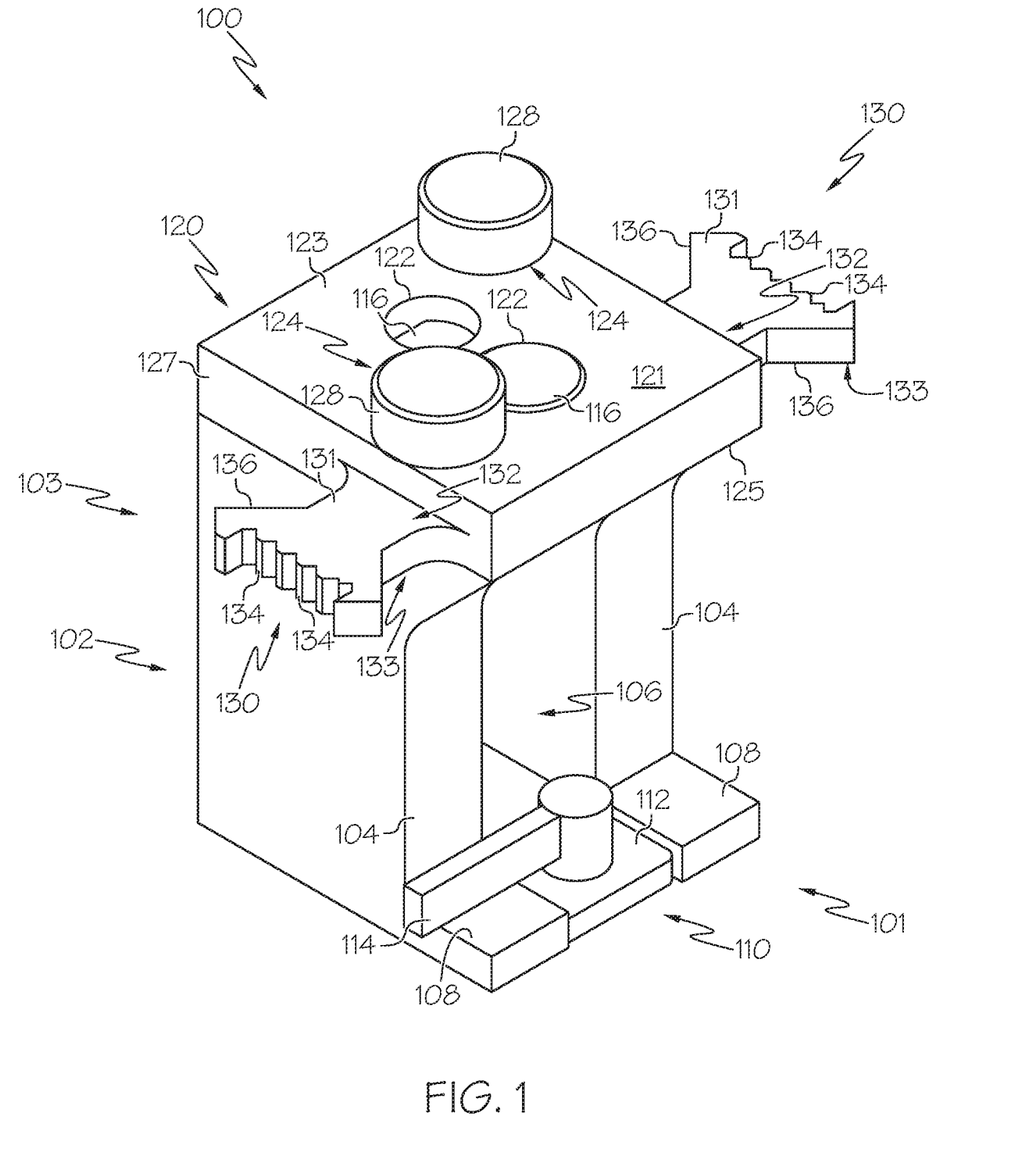
FIG. 1 is a perspective view of an exemplary graft preparation system according to one or more embodiments shown and described herein.

Referring now to FIG. 1, one embodiment of a graft preparation system 100 is depicted including a base 102 and a guide device 120 extending laterally outward from the base 102. The base 102 of the graft preparation system 100 includes a proximal end 101 and a distal end 103 positioned opposite of the proximal end 101. The base 102 further includes a pair of elongated legs 104 defining a longitudinal length of the base 102 of the graft preparation system 100. The pair of elongated legs 104 are separated from one another by an intermediate channel 106 of the base 102 formed therebetween. In particular, the intermediate channel 106 of the base 102 extends parallel to a longitudinal length of the pair of elongated legs 104 and is opened adjacent to the proximal end 101 and closed adjacent to the distal end 103. In other words, the base 102 of the graft preparation system 100 includes the intermediate channel 106 at the proximal end 101 such that the distal end 103 of the base 102 is devoid of an intermediate channel.

In this instance, the pair of elongated legs 104 of the base 102 are integrally connected to one another along the distal end 103 of the base 102 and separated from one another at the proximal end 101 by the intermediate channel 106 disposed therebetween. The pair of elongated legs 104 of the base 102 further includes at least one foot 108 extending outwardly therefrom. In particular, each of the elongated legs 104 of the base 102 includes a foot 108 integrally formed thereon and extending outwardly toward the proximal end 101. A longitudinal length of each foot 108 of the pair of elongated legs 104 extends orthogonally relative to a longitudinal length of the pair of elongated legs 104, and more specifically perpendicular. As described in greater detail herein, each foot 108 of the pair of elongated legs 104 provides a clearance and supporting surface for receiving one or more components of the graft preparation system 100, such as, for example, an engagement mechanism 110.

Still referring to FIG. 1, the intermediate channel 106 of the base 102 is sized, shaped and configured to slidably receive one or more components of the graft preparation system 100 therein, such as, for example, an engagement mechanism 110. More specifically, the engagement mechanism 110 of the graft preparation system 100 includes a sled 112 and an actuator 114 movably coupled to the sled 112. Accordingly, the intermediate channel 106 of the base 102 is sized and shaped to receive the sled 112 of the engagement mechanism 110 therein between the pair of elongated legs 104 at the proximal end 101. As briefly described above, the feet 108 of each of the pair of elongated legs 104 provides a clearance and supporting surface for receiving the actuator 114 of engagement mechanism 110 when the sled 112 is slidably received between the pair of elongated legs 104 and within the intermediate channel 106. Accordingly, the actuator 114 is configured to engage one or more of the feet 108 of the base 102 in response to an actuation of the actuator 114 of the engagement mechanism 110.

As described in greater detail herein, the engagement mechanism 110 of the graft preparation system 100 is configured to securely couple the base 102 to one or more platforms and/or working surfaces. The engagement mechanism 110 further includes one or more coupling mechanisms 116 extending outwardly from the sled 112. In particular, the one or more coupling mechanisms 116 are integrally formed with the engagement mechanism 110 and extend from the sled 114 parallel to a longitudinal length of the pair of elongated legs 104 and the intermediate channel 106 of the base 102. In this instance, the one or more coupling mechanisms 116 of the engagement mechanism 110 are sized and shaped to extend through the intermediate channel 106 between the pair of elongated legs 104 when the sled 114 of the engagement mechanism 110 is positioned therebetween.

In the embodiment, the engagement mechanism 110 includes a pair of coupling mechanisms 116 extending from the sled 114, however, it should be understood that in other embodiments additional and/or fewer coupling mechanisms 116 may be included on the sled 114. As described in detail herein, the one or more coupling mechanisms 116 of the engagement mechanism 110 are configured to couple the sled 112 to the guide device 120 and/or the base 102 of the graft preparation system 100. Although not shown, it should be understood that the sled 112 may include additional coupling mechanisms 116 extending outwardly therefrom and configured to couple the base 102 of the graft preparation system 100 to one or more platforms and/or working surfaces.

Still referring to FIG. 1, the guide device 120 of the graft preparation system 100 includes a body 121 with a top wall 123, a bottom wall 125 positioned opposite of the top wall 123, and a plurality of sidewalls 127 extending between the top wall 123 and the bottom wall 125. The body 121 of the guide device 120 is removably coupled to the base 102 of the graft preparation system 100 along the bottom wall 125. In particular, the guide device 120 includes a first plurality of apertures 122 and a second plurality of apertures 124 extending through and between the top wall 123 and the bottom wall 125. The first plurality of apertures 122 are sized, shaped and configured to receive the one or more coupling mechanisms 116 of the engagement mechanism 110. In the embodiment, the guide device 120 includes a pair of first apertures 122 corresponding to the pair of coupling mechanisms 116 of the engagement mechanism 110. Accordingly, it should be understood that in other embodiments the guide device 120 may include additional and/or fewer first apertures 122 in accordance with a quantity of coupling mechanisms 116 on the engagement mechanism 110.

With the sled 114 positioned between the pair of elongated legs 104 of the base 102 and the pair of coupling mechanisms 116 extending within the intermediate channel 106 and through the pair of first apertures 122, respectively, the engagement mechanism 110 aligns and couples the base 102 to the guide device 120. The second plurality of apertures 124 of the guide device 120 are sized, shaped and configured to receive one or more fasteners 128 therein. In the embodiment, the guide device 120 includes a pair of second apertures 124 such that each of the second apertures 124 is configured to receive at least one fastener 128 therethrough. In other embodiments, the guide device 120 may include additional and/or fewer second apertures 124 in accordance with a quantity of fasteners 128. As described in greater detail herein, the fasteners 128 are configured to securely attach the guide device 120 to the base 102 when positioned within the second apertures 124.

Still referring to FIG. 1, the guide device 120 further includes one or more suture guides 130 extending outwardly from the body 121. In particular, the one or more suture guides 130 are integrally formed with the body 121 of the guide device 120 and extend laterally outward from the sidewall 127 of the body 121 positioned between the top wall 123 and the bottom wall 125 at a predetermined length. It should be understood that the one or more suture guides 130 of the guide device 120 may extend from the body 121 at various other suitable positions, orientations, and/or configurations than those shown and described herein without departing from a scope of the present disclosure. In the embodiment, the guide device 120 includes a pair of suture guides 130 extending laterally outward from the body 121 along opposing sidewalls 127. In other embodiments, the guide device 120 may include additional and/or fewer suture guides 130.

Each of the suture guides 130 of the guide device 120 includes an elongated body 132 integrally formed with, and extending outwardly from, the sidewall 127 of the body 121. The elongated body 132 of the suture guide 130 is defined by a top interface 131, a bottom interface 133 positioned opposite of the top interface 131, and a pair of sidewalls 136. Each of the pair of sidewalk 136 extend from the elongated body 132 of the suture guide 130. As described in greater detail herein, the pair of sidewalls 136 may extend from the elongated body 132 at various angles, orientations, and/or configurations relative to the elongated body 132.

Still referring to FIG. 1, the elongated body 132 of the suture guide 130 further includes a plurality of slots 134 at a terminal end of the elongated body 132 opposite of the sidewall 127. In particular, the plurality of slots 134 of the suture guide 130 extend through the elongated body 132 between the top interface 131 and the bottom interface 133. In other words, the plurality of slots 134 of the suture guide 130 are sized and shaped to form a plurality of channels extending from the top interface 131 to the bottom interface 133. The plurality of slots 134 are positioned between the pair of sidewalls 136 of the suture guide 130. As described in detail herein, each slot 134 of the plurality of slots 134 are sized, shaped and configured to receive a medical device therethrough, such as, for example, a needle and/or a suture.

In the embodiment, a size and shape of the plurality of slots 134 of each of the suture guides 130 corresponds to a diameter of a needle and/or suture to be received therethrough. The plurality of slots 134 extending between the top interface 131 and the bottom interface 133 of each of the suture guides 130 may include various shapes and/or configurations that at least partially define a suture guide pattern of the guide device 120. In the embodiment, the plurality of slots 134 include a V-shaped configuration to facilitate centering a needle and/or suture therein. Further, the plurality of slots 134 of the guide device 120 are sequentially arranged along a longitudinal edge extending between the pair of sidewalls 136 of the suture guides 130 that further defines a suture guide pattern of the guide device 120. It should be understood that the plurality of slots 134 are offset relative one another along the longitudinal edge defined between the sidewalk 136 at a predetermined distance, and extend from the longitudinal edge and between the interfaces 131, 133 at a predetermined depth. In some embodiments, the plurality of slots 134 of one or more of the suture guides 130 may include varying sizes, shapes and/or configurations relative to one another.

Figure 2:
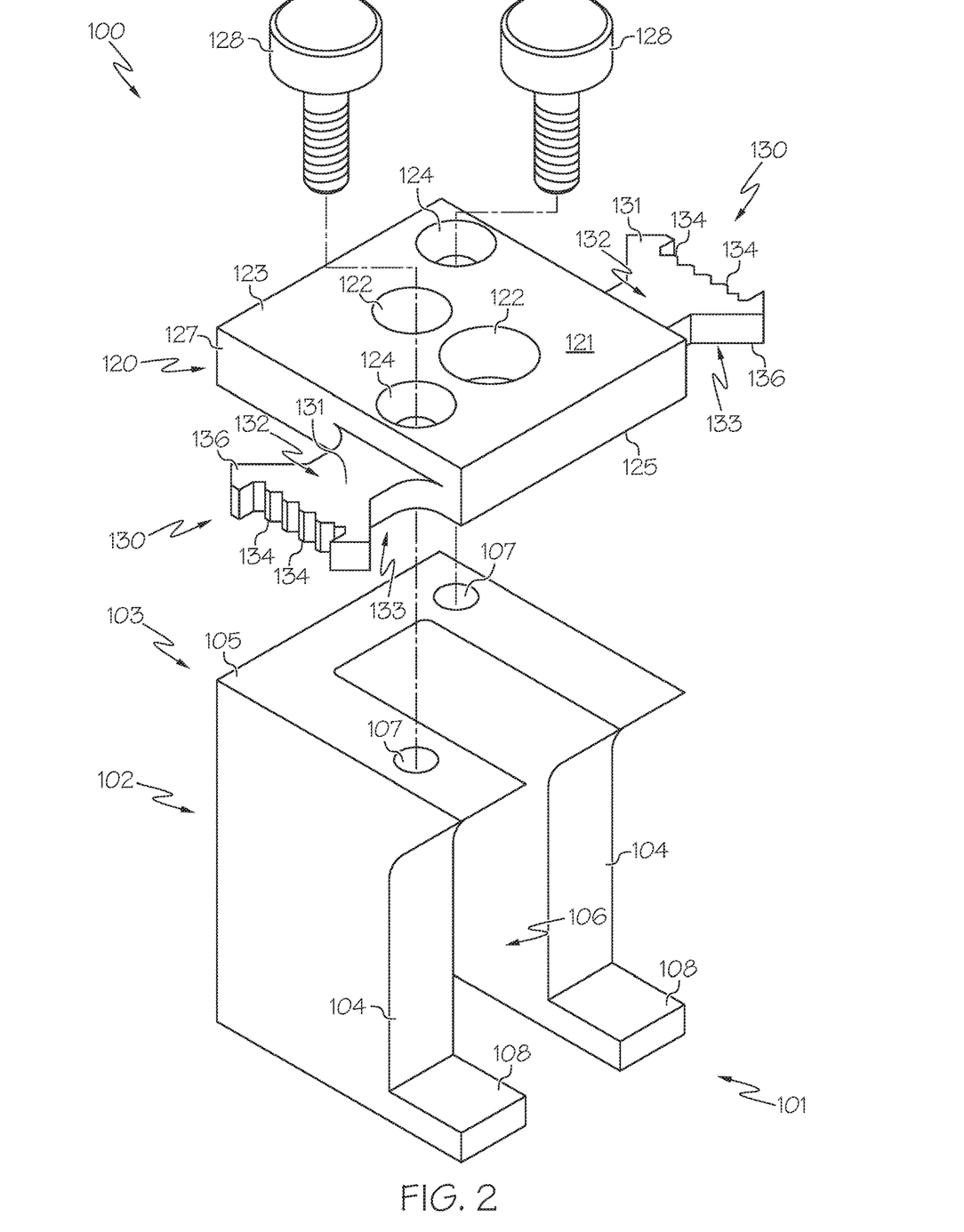
FIG. 2 is an exploded perspective view of the graft preparation system of FIG. 1 including a base and a guide according to one or more embodiments shown and described herein.

Referring now to FIG. 2, the graft preparation system 100 is schematically depicted in a disassembled state with the base 102 decoupled from the guide device 120 and the engagement mechanism 110 omitted. The base 102 of the graft preparation system 100 includes a coupling interface 105 that is sized and shaped to receive the guide device 120 thereon. In the embodiment, the guide device 120 has a lateral width defined between the sidewalls 127 that is greater than a lateral width of the base 102 as defined by the coupling interface 105 between the pair of elongated legs 104. In this instance, with the pair of suture guides 130 positioned along opposing sidewalls 127 of the guide device 120, the pair of suture guides 130 effectively extend outward relative to the base 102.

The base 102 includes one or more apertures 107 disposed along, and extending through, the coupling interface 105. A position, size and shape of the one or more apertures 107 relative to the coupling interface 105 correspond to a position, size and shape of the second apertures 124 of the guide device 120 and the one or more fasteners 128 of the graft preparation system 100. In other words, the one or more apertures 107 are configured to receive the one or more fasteners 128 therein via the second apertures 124 of the guide device 120. In the embodiment, the base 102 includes a pair of apertures 107 along the coupling interface 105 in accordance with a quantity of the second apertures 124 of the guide device 120. With the guide device 120 removably coupled to the base 102 at the coupling interface 105, the suture guides 130 of the guide device 120 are elevated relative to the base 102, and more particularly the pair of feet 108 and the pair of elongated legs 104. In other words, the base 102 is configured to position the suture guides 130 of the guide device 120 to form a clearance for receiving one or more medical devices along the bottom interface 133, such as, for example, a graft.

Still referring to FIG. 2, the pair of sidewalk 136 along the elongated body 132 of each of the suture guides 130 may extend laterally outward from the body 121 of the guide device 120 at various angles, orientations, and/or configurations. In the embodiment, the pair of sidewalls 136 of each of the suture guides 130 extend outwardly from the sidewalls 127 of the body 121 and are at least partially angled relative thereto. In particular, the pair of sidewalls 136 of the suture guide 130 are angled relative to the elongated body 132 of the suture guide 130. In other embodiments, the pair of sidewalls 136 of the suture guide 130 may include a linear profile relative to the elongated body 132 of the suture guide 130 such that the pair of sidewalls 136 are aligned parallel to the elongated body 132. As described in greater detail herein, the pair of sidewalls 136 of each of the suture guides 130 are sized, shaped and configured to guide placement and positioning of a medical device relative to the suture guide 130, such as, for example, a cutting apparatus. With the pair of sidewalls 136 of each of the suture guides 130 angularly extended relative to the sidewalls 127 of the guide device 120 and the pair of elongated legs 104 of the base 102, the guide device 120 is configured to guide placement of a medical device (e.g., a cutting apparatus) at an angled orientation relative to the base 102.

Figure 3:
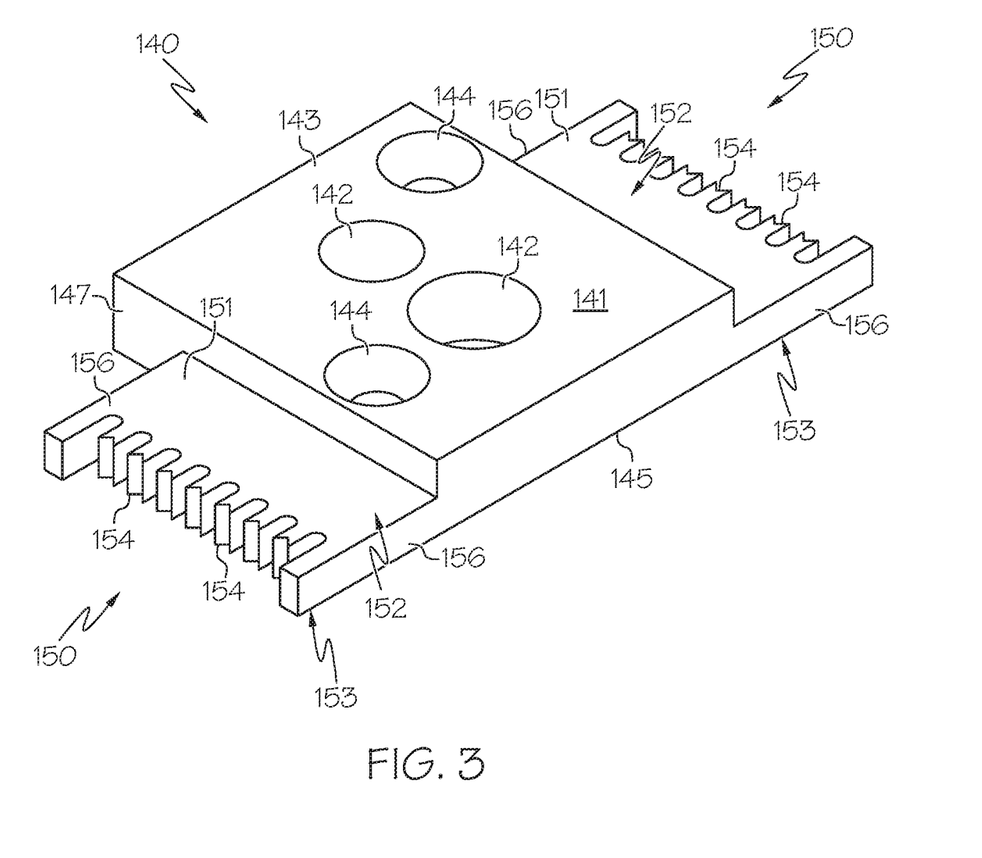
FIG. 3 is a perspective view of an alternative guide of the graft preparation system of FIG. 1 according to one or more embodiments shown and described herein.

Referring to FIG. 3, an alternative guide device 140 is schematically depicted. In the embodiment, the graft device 140 is substantially similar to the guide device 120 such that the guide device 140 may be configured and operable like the guide device 120 described above except for the differences explicitly noted herein. It should be understood that graft device 140 may be readily incorporated into the graft preparation system 100 described above as the guide device 140 functions substantially similar to the guide device 120 described above. Thus, a version of the graft preparation system 100 that is equipped with the guide device 140 may be configured and operable similar to the graft preparation system 100 equipped with the guide device 120.

For instance, the guide device 140 includes a body 141 with a top wall 143, a bottom wall 145 positioned opposite of the top wall 143, and a plurality of sidewalk 147 extending between the top wall 143 and the bottom wall 145. The body 141 of the guide device 140 may be removably coupled to the base 102 of the graft preparation system 100 along the bottom wall 145. In particular, the guide device 140 includes a first plurality of apertures 142 and a second plurality of apertures 144 extending through and between the top wall 143 and the bottom wall 145. The first plurality of apertures 142 are sized, shaped and configured to receive the one or more coupling mechanisms 116 of the engagement mechanism 110. In the embodiment, the guide device 140 includes a pair of first apertures 142 corresponding to the pair of coupling mechanisms 116 of the engagement mechanism 110. Accordingly, it should be understood that in other embodiments the guide device 140 may include additional and/or fewer first apertures 142 in accordance with a quantity of coupling mechanisms 116 on the engagement mechanism 110.

Still referring to FIG. 3, the second plurality of apertures 144 of the guide device 140 are sized, shaped and configured to receive the one or more fasteners 128 therein. In the embodiment, the guide device 140 includes a pair of second apertures 144 such that each of the second apertures 144 is configured to receive at least one fastener 128 therethrough. In other embodiments, the guide device 140 may include additional and/or fewer second apertures 144 in accordance with a quantity of fasteners 128. As described in greater detail herein, the fasteners 128 are configured to securely attach the guide device 140 to the base 102 when positioned within the second apertures 144.

The graft device 140 includes one or more suture guides 150 extending outwardly from the body 141. In particular, the one or more suture guides 150 are integrally formed with the body 141 of the guide device 150 and extend laterally outward from the sidewall 147 of the body 141 positioned between the top wall 143 and the bottom wall 145 at a predetermined length. It should be understood that the one or more suture guides 150 of the guide device 140 may extend from the body 141 at various other suitable positions, orientations, and/or configurations than those shown and described herein without departing from a scope of the present disclosure. In the embodiment, the guide device 140 includes a pair of suture guides 150 extending laterally outward from the body 141 along opposing sidewalls 147. In other embodiments, the guide device 140 may include additional and/or fewer suture guides 150.

Still referring to FIG. 3, each of the suture guides 150 of the guide device 140 includes an elongated body 152 integrally formed with, and extending outwardly from, the sidewall 147 of the body 141. The elongated body 152 of the suture guide 150 is defined by a top interface 151, a bottom interface 153 positioned opposite of the top interface 151, and a pair of sidewalls 156. Each of the pair of sidewalls 156 extend from the elongated body 152 of the suture guide 150. The elongated body 152 of the suture guide 150 further includes a plurality of slots 154 at a terminal end of the elongated body 152 opposite of the sidewall 147. In particular, the plurality of slots 154 of the suture guide 150 extend through the elongated body 152 between the top interface 151 and the bottom interface 153, and are sized and shaped to form a plurality of channels extending from the top interface 151 to the bottom interface 153. The plurality of slots 154 are positioned between the pair of sidewalk 156 of the suture guide 150.

As described in detail herein, each slot 154 of the plurality of slots 154 are sized, shaped and configured to receive a medical device therethrough, such as, for example, a needle and/or a suture. In the embodiment, a size and shape of the plurality of slots 154 of each of the suture guides 150 corresponds to a diameter of a needle and/or suture to be received therethrough. The plurality of slots 154 extending between the top interface 151 and the bottom interface 153 of each of the suture guides 150 may include various shapes and/or configurations that at least partially define a suture guide pattern of the guide device 140. In the embodiment, the plurality of slots 154 include a U-shaped configuration to facilitate centering a needle and/or suture therein.

Still referring to FIG. 3, it should be understood that the plurality of slots 154 are offset relative one another along the longitudinal edge defined between the sidewalk 156 at a predetermined distance, and extend from the longitudinal edge and between the interfaces 151, 153 at a predetermined depth that further define a suture guide pattern of the guide device 140. In some embodiments, the plurality of slots 154 of one or more of the suture guides 150 may include varying sizes, shapes and/or configurations relative to one another.

The pair of sidewalls 156 along the elongated body 152 of each of the suture guides 150 may extend laterally outward from the body 141 of the guide device 140 at various angles, orientations, and/or configurations. In the embodiment, the pair of sidewalls 156 of each of the suture guides 150 extend outwardly from the sidewalls 147 of the body 141 and include a linear profile relative to the elongated body 152 of the suture guide 150, such that the pair of sidewalls 156 are aligned parallel to the elongated body 152 and perpendicular to the sidewalls 147 of the guide device 140 and the pair of elongated legs 104 of the base 102. As described in greater detail herein, the pair of sidewalls 156 of each of the suture guides 150 are sized, shaped and configured to guide placement and positioning of a medical device relative to the suture guide 130, such as, for example, a cutting apparatus.

With the pair of sidewalls 156 of each of the suture guides 150 extending perpendicular relative to the pair of elongated legs 104 of the base 102 (see FIG. 1), the guide device 140 is configured to guide placement of a medical device (e.g., a cutting apparatus) at a perpendicular orientation relative to the base 102.

Figure 4:
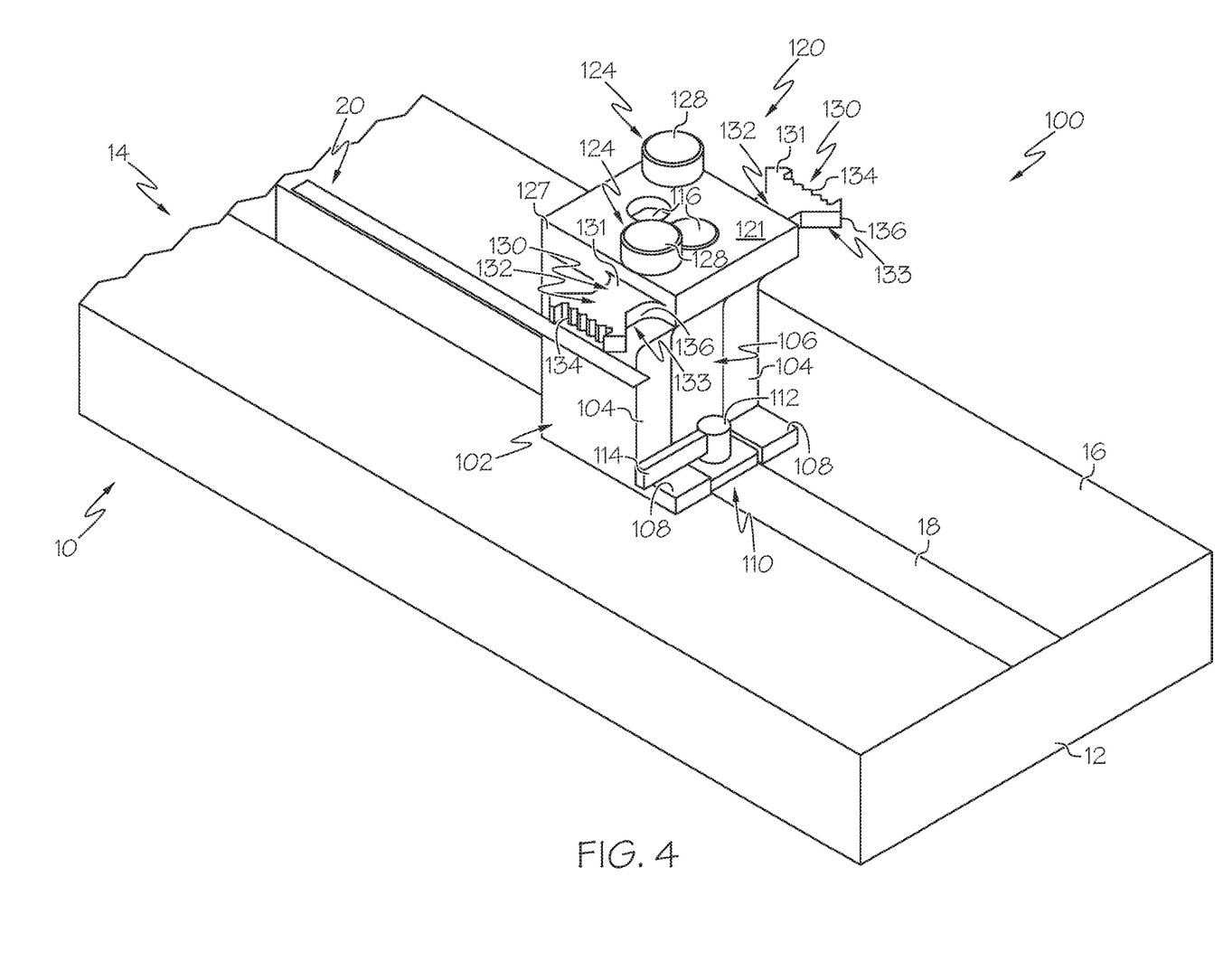
FIG. 4 is a perspective view of the graft preparation system of FIG. 1 coupled to a working platform according to one or more embodiments shown and described herein.

Referring now to FIG. 4, the graft preparation system 100 is schematically depicted coupled to a working surface 10 for suturing a graft. The graft preparation system 100 is operable to augment a graft (e.g., tendon graft, ligament graft, allograft, etc.) and facilitate a placement, spacing, tensioning and fixation of a suture(s) within the graft by providing guiding features for preparing a pre-sutured graft. The depiction of FIG. 4 and the accompanying description below is not meant to limit the subject matter described herein or represent an exact description of how the graft preparation system 100 provides preparation of a graft, but instead is meant to provide a simple schematic overview to illustrate suturing a graft with graft preparation system 100 described herein.

Initially, the graft preparation system 100 is positioned along the working surface 10 that includes a proximal end 12, a distal end 14 positioned opposite of the proximal end 12, and a top surface extending therebetween. In the embodiment, the working surface 10 further includes a channel 18 disposed between the proximal end 12 and the distal end 14 and extending along a longitudinal length of the working surface 10. The channel 18 is exposed along the top surface 16 of the working surface 10 and is sized, shaped and configured to receive the graft preparation system 100 therein. In particular, with the base 102 of the graft preparation system 100 received along the top surface 16 of the working surface 10, the intermediate channel 106 is aligned with the channel 18. The pair of feet 108 of the base 102 abut against the top surface 16 and are positioned about the channel 18 with the intermediate channel 106 positioned over the channel 18. In this instance, the graft preparation system 100 may be selectively moved and positioned along the working surface 10 at a desired location prior to the insertion and/or actuation of the engagement mechanism 110. In other words, the base 102 of the graft preparation system 100 is slidably translatable relative to the working surface 10 when the engagement mechanism 110 is in an unlocked state.

Still referring to FIG. 4, with the base 102 positioned at a desired location relative to the top surface 16 of the working surface 10, the engagement mechanism 110 may be inserted into and at least partially positioned within the intermediate channel 106 of the graft preparation system 100 and the channel 18 of the working surface 10, in this instance, actuation of the actuator 114 of the engagement mechanism 110 securely couples the base 102 to the top surface 16 and transitions the graft preparation system 100 to a locked state with the working surface 10. In particular, one or more coupling mechanisms 116 extending from the engagement mechanism 110 may engage the channel 18 of the working surface 10 thereby securely coupling the base 102 thereto.

Accordingly, a relative position of the graft preparation system 100 along the working surface 10 is fixed. The guide device 120 may be received over the coupling interface 105 of the base 102 (see FIG. 3) such that the one or more coupling mechanisms 116 of the engagement mechanism 110 are slidably received through the first plurality of apertures of the body 121. In this instance, a position and orientation of the guide device 120 is fixed relative to the base 102. Insertion of the one or more fasteners 128 through the second plurality of apertures 124 of the body 121, and receipt within the corresponding one or more apertures 107 of the base 102 (see FIG. 3), securely attaches the guide device 120 to the base 102. In this instance, the guide device 120 is removably coupled to the body 121 such that the guide device 120 is selectively removable from the body 121 in response to removal of the one or more fasteners 128 from the second plurality of apertures 124.

Still referring to FIG. 4, with the graft preparation system 100 securely coupled to the working surface 10, the bottom interface 133 of the guide device 120 removably receives a graft 20 thereon. In other words, the graft 20 is positioned in alignment with the suture guide pattern defined by the plurality of slots 134 of at least one of the suture guides 130. The guide device 120 is configured to facilitate placement of a suture (not shown) from the top interface 131 into at least one of the plurality of slots 134 such that the suture is received through the graft 20 at the bottom interface 133. In other words, with a suture secured to a needle (not shown), the needle and suture are slidably received at (e.g., inserted into) the suture guide 130 of the guide device 120 from the top interface 131, through at least one channel formed by at least one of the plurality of slots 134, and out at the bottom interface 133. With the graft 20 positioned adjacent to and/or against the bottom interface 133 of the suture guide 130, the suture and needle are received through the graft 20 at a first suture location.

Repeatedly inserting the needle and the suture through each of the plurality of slots 134 of the suture guide 130 provides sequential suturing locations along the graft from a second suture location to a plurality of suture locations in accordance with a location and quantity of the plurality of slots 134. Accordingly, the second suture location is laterally offset relative to the first suture location due to a lateral offset of at least a first slot 134 of the plurality of slots 134 from a second slot 134 of the plurality of slots 134. As described in greater detail above, a lateral offset between the suture locations along the graft 20 is based on a predetermined distance between each of the plurality of slots 134. Accordingly, sequentially inserting the needle and the suture attached thereto through each of the plurality of slots 134 provides suturing the graft 20 at a plurality of suture locations at a lateral offset that is based on the predetermined distance of the suture guide pattern defined by the plurality of slots 134.

Still referring to FIG. 4, with the graft 20 having received the suture therethrough at a plurality of suture locations in accordance with the suture guide 130 of the guide device 120, a cutting apparatus (not shown) is aligned with at least one of the sidewalls 136 of the suture guide 130 to guide placement of the cutting apparatus relative to the graft 20 received along the bottom interface 131. As described in detail above, the pair of sidewalls 136 of each of the suture guides 130 are configured to facilitate placement of a medical device (e.g., a cutting apparatus) relative to the graft 20 positioned along the bottom interface 131 of the suture guide 130. Accordingly, upon completing a suturing of the graft 20 a cutting apparatus may be aligned with at least one of the sidewalls 136 to guide placement of the cutting apparatus relative to the graft 20 for ablation. Although the guide device 120 is shown and described in the exemplary description herein, it should be understood that the guide device 140 (see FIG. 3) may be readily incorporated and used with the graft preparation system 100 to suture and ablate the graft 20 in a substantially similar manner.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

For the purposes of describing and defining the present invention it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A graft preparation system comprising:
   a base;
   a guide extending laterally outward from the base and including a top interface and a bottom interface, wherein the bottom interface removably receives a graft thereon;
   a plurality of slots extending through the guide between the top interface and the bottom interface, wherein each slot of the plurality of slots are sized to receive a needle therethrough such that the plurality of slots form a plurality of channels from the top interface to the bottom interface;
   wherein the guide is configured to facilitate placement of a suture attached to the needle from the top interface into at least one of the channels formed by the plurality of slots such that the suture is received through the graft at the bottom interface.

2. The graft preparation system of claim 1, wherein the guide is removably coupled to the base such that the guide is selectively removable from the base.

3. The graft preparation system of claim 2, wherein the guide includes one or more apertures sized and shaped to receive one or more fasteners therethrough to couple the guide to the base.

4. The graft preparation system of claim 3, wherein the one or more coupling features extend from an engagement mechanism received within the base, the engagement mechanism is further configured to securely fix the base to a working surface when in a locked state.

5. The graft preparation system of claim 4, wherein the base is slidably translatable relative to the working surface when the engagement mechanism is in an unlocked state.

6. The graft preparation system of claim 1, wherein the guide is elevated relative to one or more feet of the base such that the base is configured to position the guide to form a clearance for receiving the graft along the bottom interface.

7. The graft preparation system of claim 1, wherein the guide includes a pair of sidewalls extending laterally outward from the base, the sidewalls are sized and shaped to guide placement of a cutting apparatus relative to the graft received along the bottom interface.

8. The graft preparation system of claim 7, wherein the pair of sidewalls extend perpendicularly relative to the base such that the guide is configured to guide placement of the cutting apparatus at a perpendicular orientation relative to the base.

9. The graft preparation system of claim 7, wherein the pair of sidewalls extend at an angle relative to the base such that the guide is configured to guide placement of the cutting apparatus at an angled orientation relative to the base.

10. The graft preparation system of claim 1, further comprising a second guide extending laterally outward from the base opposite of the guide.

11. The graft preparation system of claim 1, wherein a size and shape of the plurality of slots corresponds to a diameter of the suture to be received therethrough.

12. The graft preparation system of claim 1, wherein the plurality of slots extending through the guide between the top interface and the bottom interface are V-shaped or U-shaped to facilitate centering the needle received therethrough.

13. The graft preparation system of claim 1, wherein the plurality of slots are sequentially arranged along a longitudinal edge of the guide, the plurality of slots are offset relative one another along the longitudinal edge at a predetermined distance and extend from the longitudinal edge toward the base at a predetermined depth.

14. A suture guide device for preparing a ligament graft, comprising:
  a base including a coupling interface;
  a guide coupled to the base at the coupling interface, the guide having a width greater than the coupling interface and including a pair of suture guide patterns at opposing sides of the guide such that the pair of suture guide patterns extend outward relative to the base, the pair of suture guide patterns define a top interface and a bottom interface, wherein the bottom interface is operable to receive a graft thereon; and
  a plurality of slots extending through the pair of suture guide patterns between the top interface and the bottom interface, wherein each slot of the plurality of slots are sized to receive a needle therethrough;
  wherein the guide is configured to facilitate placement of a suture attached to the needle through at least one of the plurality of slots of the suture guide patterns such that the suture is received through the graft positioned along the bottom interface.

15. The suture guide device of claim 14, wherein at least one of the pair of suture guide patterns has a pair of angled sidewalls, the pair of angled sidewalls is configured to facilitate placement of a cutting apparatus relative to the graft positioned along the bottom interface of the suture guide pattern.

16. The suture guide device of claim 14, wherein the plurality of slots of at least one of the pair of suture guide patterns includes varying sizes or shapes relative one another.

17. The suture guide device of claim 14, wherein the base is slidably coupled to a working surface such that the base is translatable along the working surface.

18. A method for preparing a ligament graft with a suture guide device, the method comprising:
  positioning the ligament graft along a bottom interface of a guide pattern of the suture guide device;
  inserting a needle with a suture attached thereto through a first slot of a plurality of slots extending through the guide pattern from a top interface that is opposite of the bottom interface such that the needle is received through the ligament graft positioned along the bottom interface of the guide pattern at a first suture location; and
  inserting the needle with the suture attached thereto through a second slot of the plurality of slots extending through the guide pattern from the top interface such that the needle is received through the ligament graft at a second suture location, wherein the second slot is laterally offset from the first slot at a predetermined distance such that the second suture location is separated from the first suture location by the predetermined distance.

19. The method of claim 18, further comprising repeatedly inserting the needle with the suture attached thereto sequentially through each of the plurality of slots of the guide pattern such that the ligament graft includes the suture through a plurality of suture locations along the ligament graft.

20. The method of claim 19, further comprising aligning a cutting apparatus with a sidewall of the guide pattern to guide placement of the cutting apparatus relative to the ligament graft received along the bottom interface.

* * * * *